United States Patent [19]

Greenshields et al.

[11] Patent Number: 5,633,032

[45] Date of Patent: May 27, 1997

[54] PROCESS OF PREPARING CEREAL EXTRACTS

[75] Inventors: Roderick N. Greenshields, Swansea, Great Britain; Artis L. Rees, Port Talbot, Wales

[73] Assignee: CPC International Inc, Englewood Cliffs, N.J.

[21] Appl. No.: 244,036

[22] PCT Filed: Nov. 16, 1992

[86] PCT No.: PCT/GB92/02122

§ 371 Date: Feb. 10, 1995

§ 102(e) Date: Feb. 10, 1995

[87] PCT Pub. No.: WO93/10157

PCT Pub. Date: May 27, 1993

[30] Foreign Application Priority Data

| Nov. 16, 1991 | [GB] | United Kingdom | 9124427 |
| Mar. 12, 1992 | [GB] | United Kingdom | 9205406 |
| Apr. 27, 1992 | [GB] | United Kingdom | 9209094 |
| Nov. 16, 1992 | [GB] | United Kingdom | 9214392 |

[51] Int. Cl.$^6$ .................................................. A23L 1/28
[52] U.S. Cl. .................. 426/618; 426/425; 426/431; 426/436; 426/478
[58] Field of Search ......................... 426/618, 425, 426/431, 436, 478, 634

[56] References Cited

U.S. PATENT DOCUMENTS

| 4,927,649 | 5/1990 | Antenucci | 426/273 |
| 5,057,334 | 10/1991 | Vail | 426/634 |

Primary Examiner—Esther Kepplinger
Assistant Examiner—Lien Tran
Attorney, Agent, or Firm—Brooks Haidt Haffner & Delahunty

[57] ABSTRACT

Two cereal extracts are produced by means of a process comprising the steps of milling cereal material, suspending the milled material in an aqueous liquid, treating the suspension with an alkali, acidifying and separating the solid and liquid in the resulting mixture. The liquid and solid may be further purified and are useful as ingredients in comestible products.

2 Claims, No Drawings

PROCESS OF PREPARING CEREAL EXTRACTS

BACKGROUND OF THE INVENTION

This invention relates to a process for producing cereal extracts.

The use of corn bran extracts as bulking agents in food products is well-known. U.S. Pat. No. 4,927,654 discloses a process for producing hemicellulose extracts from delignified plant fibres, such as corn bran, by extracting the plant fibres with sodium hydroxide solution and acidifying the resulting mixture to precipitate a first hemicellulose fraction. A second hemicellulose fraction is precipitated from the resulting filtrate by the addition of ethanol.

The present invention provides a process for producing two novel extracts from cereal-derived material.

SUMMARY OF THE INVENTION

A first cellulose-containing extract may be obtained by the following process. The extract may be produced as an insoluble bleached cellulose residue of alkaline extracted cereal material (e.g., cell walls of maize bran) and may contain other insoluble biopolymers besides cellulose.

DETAILED DESCRIPTION OF THE PREFERRED EMBODIMENTS

Accordingly, the present invention provides a process for producing a cellulose-containing cereal extract produced by the process comprising the steps of:

(i) milling cereal material;
(ii) suspending the milled cereal material in an aqueous liquid;
(iii) treating the resulting suspension with an alkali;
(iv) lowering the pH of the treated suspension to from 5 to 7;
(v) separating the solids and the liquid in the resulting mixture;
(vii) treating the solids with hydrogen peroxide;
(vii) washing the treated solids; and
(viii) optionally drying the washed solids.

The cereal material is preferably milled (either in wet or dry form) to a particle size of from 50 to 250 μm e.g., 80 to 180 μm. The aqueous liquid in which the milled cereal material is suspended is preferably water but may also be a solution or a suspension of other substances in water provided that this does not adversely interfere with the subsequent steps in the process. The suspension preferably contains from 5 to 10% (e.g., 8%) dry weight/volume of milled corn bran and may be formed at ambient temperature.

The cereal material is preferably cereal husk or bran and may be obtained from cereals such as maize, corn, barley, wheat, rice or oats, or malt or malt culms. Preferably the cereal material is corn bran. The milled material may be air classified or sieved to remove starch and the starch removal process may comprise starch removal by suitable enzyme treatment, for example, with diatase (alpha- or beta-amylase).

Many alkalis may be used to effect the alkaline treatment step (step (iii)) of the process e.g., metal hydroxides such as sodium and potassium hydroxides or metal carbonates such as sodium or calcium carbonate. Preferably, potassium hydroxide (e.g., in the form of a solid) is added to the suspension to provide a concentration of not less than 4% w/v of KOH. The mixture may be stirred to dissolve the potassium hydroxide. This is accompanied by a colour change to bright yellow or orange. The mixture is preferably heated to from 70° to 80° C. for from 1½ to 2½ hours in order to effect maximum extraction or until a rapid increase in viscosity is noticed. The reaction mixture is then adjusted to a pH of from 5 to 7 (e.g., neutral pH) with an acid (e.g., dilute or concentrated hydrochloric acid). This may be accompanied by a visible paling in colour and "clouding" of the material. The extract is preferably separated from the insoluble material by filtration through a coarse filter (e.g., grade 0 sintered glass at lab scale/5–50 um plastic mesh on larger scale) with the application of partial vacuum or by centrifugation.

The insoluble material may be washed in situ on the filter with warm water to give the desired degree of extraction. Extraction by this process typically yields 45–55% of the dry weight of the material.

The insoluble material obtained from alkali extraction of the hemicellulosic material after step (v) may be resuspended in water to give a from 2 to 5%, preferably from 2.5 to 3.0% w/v, suspension in water. The pH is adjusted to from 12 to 13 (preferably 12.5) preferably by adding 40% w/v potassium hydroxide solution.

After raising the temperature (e.g., to from 70° to 75° C.) in an indirectly heated vessel, hydrogen peroxide (e.g., 30 volume or 10 volume) is added preferably in an amount such that the peroxide is present at an amount of from 15 to 20% dry wt/dry wt insoluble material. The temperature is maintained, with gentle stirring, at an elevated temperature, preferably from 70° to 80° C. (such as from 70° to 75° C.) for from 2 to 5 hours (e.g., 3–4 hours). Allowance should be made in the capacity of the vessel for up to 20% foaming on addition of peroxide. The suspension may be stored for some days at this stage without loss or damage.

Following the reaction with peroxide, the pH of the suspension is lowered to below 7 (e.g., from 5.5 to 6.0) with an acid such as hydrochloric acid. Solubilised material is preferably removed by filtration under partial vacuum. (Grade 0 sintered glass filter on laboratory scale, 5–50 μm plastic mesh on larger scale).

The insoluble material may then be washed on the filter with water, preferably with at least 3 volumes of water. The washed material may be stored aseptically, or suspended and spray dried.

This extract can be used as a bulking agent in foodstuffs but also possesses lipomimetic properties.

The hemicellulose-based extract obtained in the extraction process may be purified in the following manner:

1 Extracts and washings are combined and diluted such that the total dissolved solids are in the region of 2.5% w/v.

2 The diluted extract is applied to a tangential flow ultrafiltration apparatus. (Under the following conditions during a pilot scale trial).
  Starting volume 100 liters
  Membrane area 6 m$^2$
  Membrane configuration parallel tubes
  Membrane type polysulphone 15,000 mwco
  Average flux rate 9 to 10 liters m$^{-2}$.h$^{-1}$
  Run time 85 min The concentrated retentate was diluted with 30 l of water and the operation repeated three times before the solids Content of the filtrate approaches zero.

Further decolourisation and deodorisation may be achieved by passing the diluted desalted filtrate over a carbon column containing Anthrosorb for odour removal and Norit C for colour removal.

The extract which at this stage is quite viscous may be dried by freeze drying, vacuum drying or spray drying. The extract is essentially an alkali-soluble complex hemicellulose mixture.

The extract may be used as a bulking agent or a thickening agent (e.g., in food products) and has adhesive properties.

The present invention thus allows the production of both an insoluble polysaccharide and an alkali soluble polysaccharide which may be used as food ingredients.

What is claimed is:

1. A method of producing a cellulose-containing cereal extract comprising the steps of:
   (i) milling cereal material;
   (ii) suspending the milled cereal material in an aqueous liquid;
   (iii) treating the resulting suspension with an alkali for a period of from 1.5 to 2.5 hours at a temperature from 70° to 80° C.;
   (iv) lowering the pH of the treated suspension to from 5 to 7;
   (v) separating the solids and the liquid in the resulting suspension;
   (vi) treating the solids with hydrogen peroxide;
   (vii) washing the treated solids; and
   (viii) optionally drying the washed solids.

2. A method of producing a cellulose-containing cereal extract comprising the steps of:
   (i) milling cereal material;
   (ii) suspending the milled cereal material in an aqueous liquid;
   (iii) treating the resulting suspension with an alkali for a period of from 1.5 to 2.5 hours at a temperature from 70° to 80° C.;
   (iv) lowering the pH of the treated suspension to from 5 to 7;
   (v) separating the solids and the liquid in the resulting suspension;
   (vi) treating the solids with hydrogen peroxide by a process comprising the steps of:
      (a) resuspending the separated solids in an aqueous liquid;
      (b) raising the pH of the resulting suspension to a pH from 12.2 to 12.5;
      (c) treating the suspension with hydrogen peroxide;
      (d) lowering the pH of the suspension to below 7; and
      (e) separating the solids from the suspension;
   (vii) washing the treated solids; and
   (viii) optionally drying the washed solids.

* * * * *